United States Patent [19]

Detronde

[11] Patent Number: 4,671,674
[45] Date of Patent: Jun. 9, 1987

[54] PROCESS FOR THE DETECTION AND RECORDING OF WEAK POINTS OR DEFECTS ON HOT IRON AND STEEL INDUSTRY SEMIFINISHED PRODUCTS

[75] Inventor: Michel Detronde, Maidieres, France
[73] Assignee: Somafer, Fameck, France
[21] Appl. No.: 822,306
[22] PCT Filed: Apr. 24, 1985
[86] PCT No.: PCT/FR85/00093
 § 371 Date: Dec. 20, 1985
 § 102(e) Date: Dec. 20, 1985
[87] PCT Pub. No.: WO85/04956
 PCT Pub. Date: Nov. 7, 1985

[30] Foreign Application Priority Data

Apr. 24, 1984 [FR] France .................. 84 06759

[51] Int. Cl.$^4$ .............. G01N 21/00; G01N 25/72
[52] U.S. Cl. ..................... 374/5; 340/577; 358/113; 374/124; 374/8; 382/48
[58] Field of Search .......... 374/8, 5, 124, 153, 374/139; 358/113; 340/577; 382/48

[56] References Cited

U.S. PATENT DOCUMENTS

| | | | |
|---|---|---|---|
| 2,260,186 | 10/1941 | McNutt | 374/5 |
| 3,148,531 | 9/1964 | Stoll et al. | 374/8 X |
| 3,665,750 | 5/1972 | Dawn et al. | 374/8 |
| 3,718,757 | 2/1973 | Gulitz et al. | 358/113 |
| 4,144,758 | 3/1979 | Roney | 374/129 |
| 4,215,562 | 8/1980 | Gavrilin et al. | 374/5 |
| 4,219,844 | 8/1980 | Ohsumi et al. | 374/101 X |
| 4,247,306 | 1/1981 | Berge | 374/5 |
| 4,439,049 | 3/1984 | Hoogendoorn et al. | 374/5 X |
| 4,502,793 | 3/1985 | Smith et al. | 374/124 |
| 4,539,588 | 9/1985 | Ariessohn et al. | 374/124 X |
| 4,551,030 | 11/1985 | Lunkkala et al. | 374/5 |

FOREIGN PATENT DOCUMENTS

| | | |
|---|---|---|
| 833244 | 12/1975 | Belgium . |
| 2381304 | 9/1978 | France . |
| 0587378 | 1/1978 | U.S.S.R. ............... 374/8 |

OTHER PUBLICATIONS

Publication: "Determining the Dynamic Oxygen Content Index of Insulated Fine Wire", by Angelo et al., IBM 1977, p. 4107-4108.

Primary Examiner—Daniel M. Yasich
Attorney, Agent, or Firm—Dennison, Meserole, Pollack & Scheiner

[57] ABSTRACT

The present invention relates to a process for the detection and recording of the weak points or defects on hot semifinished iron and steel industry products, by application of the flame of an oxygen-supplied blowtorch to the surface to be examined, displacing the application point along the surface, picking up the image of the application point by video camera, and transmitting the image to a remote location. An observer viewing this screen can make a map of the surface examined, recording thereon the weak points or defects detected both by their dimensions and by their type. This process finds application in the hot treatment of the slabs, blooms, and steel rods, when the casting, defect repair and rolling operations are to be carried out continuously.

6 Claims, 3 Drawing Figures

PROCESS FOR THE DETECTION AND RECORDING OF WEAK POINTS OR DEFECTS ON HOT IRON AND STEEL INDUSTRY SEMIFINISHED PRODUCTS

BACKGROUND OF THE INVENTION

The present invention relates to a process for the detection and recording of defects and/or weak points on hot semifinished iron and steel industry products.

Iron and steel industry semifinished products such as slabs, blooms, steel rods, which are obtained from ingot casting or from continuous casting, are generally transformed into flat products by hot rolling.

In an action allowing energy savings and decreased production costs, the iron and steel industry seeks maximum benefit from the heat of casting of semifinished products, to effect the subsequent rolling operation. However, the semifinished products can have visible or invisible defects or weak points, in the vicinity of their surfaces, which are fissures, tears, folds or some other defect type, which risk remaining on the rolled products or even being amplified and causing rejection of the piece, or even damage of the surface of the roller cylinders. That is why it has proven necessary to examine the semifinished products before proceeding with rolling, to determine whether they can be rolled directly or whether they must be treated beforehand to delete or repair the defects which they have, or even if they are of such low quality that they must be recycled.

Until this time, because of the processes and materials used, this examination for the detection of the weak points or defects required precooling of the semifinished products; this led the iron and steel industry to seek ways to do this and to save energy. Studies have consequently been undertaken by the iron and steel industry in Europe, the United States and Japan to find a method which will allow detection and repair of the weak points or defects in the product, the method being such that it can where desired be introduced into the chain of casting and rolling operations, so as to realize an entirely continuous process.

Because the semifinished products are hot, the observer cannot examine them directly. All of the studies undertaken until this time have therefore been based on the principle of forming an image of the weak points or defects from a distance, which will then serve as guide for the automatic repair. To apply this principle, an entire series of more or less sophisticated processes have been designed, which differ both in the means of obtaining the image and in the means of recording this image and using this recording to effect the repair of the semifinished products.

But these processes, besides the fact that they require a long and difficult installation, generally present drawbacks, particularly in the detection of the weak points or defects. In fact, the image which is obtained is not the reflection of what an observer might see, but most often is a collection of points obtained from the physical features which are expected to represent the "health" of the semifinished products. Because of this, it is practically impossible for the observer to distinguish between the points which actually correspond to the state of the semifinished products and the points resulting from disturbance of the transmission of signals issuing from these features; the faculty of interpretation and the judgment of the observer is thus practically inconsequential. The recording of such images and the use of such images by the repairer can then lead to nonuniform semifinished products being fed into rolling.

Each of these processes also presents specific deficiencies. Thus, for example, according to the type of detection which is used, it is observed that:

The use of a camera and infrared television gives images disturbed by the presence of powders which are for lubrication of the ingot molds, oxidation spots, and irregularities of surface due to oscillation of the ingot molds, which makes analysis difficult. Moreover, these systems give no indication at all of the depth of the defects or weak points.

The use of television and Foucault currents allow visualization of the weak points or defects in depth but along only short lengths (1 to 5 mm).

The electromagnetic and ultrasonic systems are sensitive to metallurgical transformations in the vicinity of the Curie point (600 to 700 degrees C.) which disturb the transmission of waves and lead to parasitic effects. They also require deoxidation beforehand of the surfce of the semifinished products to allow a suitable transducer-steel coupling.

The induction preheating and infrared detection systems give results which are controlled by the angle of the defect in relation to the measurement axis; transverse defects or defects which present angles less than 15 degrees in relation to the transverse axis are poorly detected.

SUMMARY OF THE INVENTION

Faced with the problems posed by each of these techniques, the applicant has sought and disclosed a relatively simple process and means for detection which lead to an image which actually and very faithfully reflects the macrostructure of the surface of the semifinished products and, from that, the operator can continue to play the role of observer and interpreter of the weak points and defects has been done for examination of the cold semifinished products.

The applicant has combined image recording means with these detection means, which allow the repairer to intervene efficiently and uniquely where the surface of the semifinished products is effectively defective.

This detection and recording process of the defects or weak points on hot semifinished products of the iron and steel industry is characterized in that the flame of an oxygen-supplied blowtorch is applied at a certain angle to the plane of the surface to be examined, that the point of application is moved at a certain speed, and that the image of the points of application is picked up by a video camera and transmitted to a remote location, where an observer viewing this image can establish a plot of the examined surface by recording thereon the dimensions and type of weak points or defects detected.

DETAILED DESCRIPTION OF THE INVENTION

Figure 1:
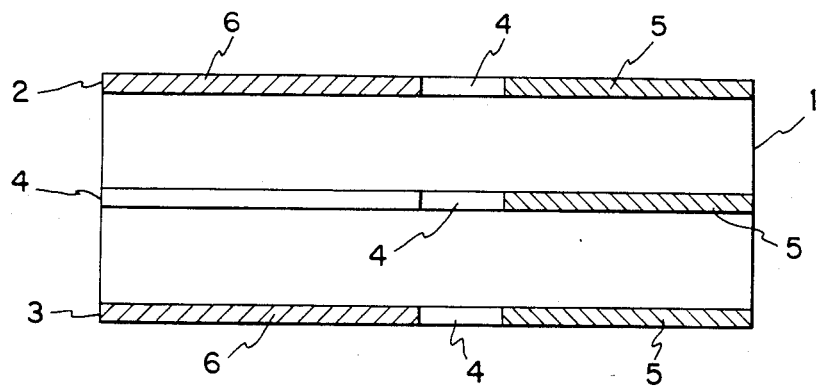
FIG. 1 is a plan view of a semifinished product treated according to the method of the present invention.

The process according to the invention first consists of application of the flame of an oxygen-supplier blowtorch to the surface to be examined, and displacement of its application point on this surface. With these conditions, under the initial effect of the flame, the surface of the semifinished product is heated and brought to a temperature such that, as a result, the application of oxygen alone, because of the exothermicity of its reaction with iron, suffices to form a bath of molten metal on the surface at the application point. Under the effect of the kinetic energy of the oxygen, the molten metal is blown continuously so that the metal is removed at the site. This removal is a function of the duration of exposure of the surface to the flame, and the depth of the bath for a given blowtorch will depend on its speed of displacement. Generally speaking, conditions are created which permit depth of bath, i.e. thickness of removed metal, of 1 to 2 mm.

In the course of this movement on the surface of the semifinished product, when the flame comes to be applied on a weak point or a defect which opens at the surface, the application of heat becomes excessive at this site because of the discontinuity in the metal mass, due to the oxidation of the iron, and causes a local overheating of the metal. This overheating is translated by the appearance of a white spot which is detached on the bottom of the yellow colored bath. By observation of the white spots, it is possible to obtain a very precise indication of the presence of defects or weak points in the surface of the semifinished products. Moreover, because the overheating and therefore the spot exist because there is a discontinuity, then by following the shape of the spot, it is possible to learn the dimensions of the defect and its orientation in relation to the direction of the flame. Besides, as the work is done at a constant rate of speed of the blowtorch, and thus to a constant depth of bath, if the defect is still deeper than the thickness of the metal which is removed, the spot will persist and there is thus an indication of the depth of the defects.

When the defects do not emerge at the surface of the semifinished product, such as inclusions or bubbles, then they are detected following removal of the metal at the moment when the discontinuity reaches the surface and is manifested likewise by the appearance of white spots.

The blowtorch is thus a means which not only permits detection of the defects or weak points, but also allows the determination of their type and their surface and depth dimensions.

Most of the known torches, whether they are round or multi-sided, can be used for detection. Simple adaptations are necessary only in certain cases.

To obtain good examination results, the apparatus is generally arranged to have zones of application of the torch to the semifinished product which are of approximately 300 to 500 $mm^2$ surface area, and the axis of the torch is inclined at an angle of between 5 and 15 degrees in relation to the surface to be examined. The speed of displacement of the torch is preferable between 15 and 20 m/minute.

It is also possible to control the oxygen flow to obtain the desired depth of bath.

Because of the application of the process to a hot semifinished product with great heat radiation, it is not possible to manipulate the torch at the examination site. That is why it is usually placed on a gantry crane over the semifinished product and controlled by remote control. The point of application of the torch in relation to the surface being examined can be moved by moving the gantry crane or by holding the crane stationary while the semifinished product is moved under the torch. This last arrangement can be applied to semifinished products which are precut and placed on the conveyor belt, but it is particularly adapted to the treatment of semifinished products in continuous casting.

Considering that the semifinished products can have widths of several meters, and the width of the impact of the torch is 5 to 6 cm at the most, it can be conceived that it will be necessary to provide a plurality of blowtorches or to provide a systematic sweeping of the surface to be examined with one single torch to obtain complete detection. This is no problem because statistical studies show that, on the one hand, the inclusionary state depends upon casting conditions, and on the other hand, the tears and defects which open at the surface are due either to the composition of the cast semifinished product, or else to the mechanical holding means, as well as other factors which act in the same manner. Consequently, for a semifinished product of relatively small width, it generally suffices to use one single torch, and for semifinished products which are wider, to use three torches at the most, of which two are placed near the edges and the third halfway between the edges.

In the course of the movement of the semifinished product, the point or points of application of the torch or torches thus describe lines parallel to the length of the semifinished product and this product is thus examined solely along lengthwise strips. By extrapolation, this examination which is thus limited allows the faithful reconstitution of the state of the entire surface of the semifinished product. However, if the quality of the semifinished product requires it, it is necessary to multiply the number of strips examined. This is easily realized because it is possible to move the torch at a speed 10 to 20 times faster than the rate of forward movement of the semifinished product.

For the same reasons of symmetry, examination of the semifinished product is generally limited to one single surface of the semifinished product which is the top or bottom face in the case of a continuous casting.

However, in addition to the movement of the torch or torches due to the movement of the gantry crane or the semifinished product, the torch can be tilted differently in relation to the examined surface, at an angle which must be known and considered in the interpretation of the defect or weak point. The torch is also actuated in a sweeping movement transverse to the direction of its movement or displacement so as to be able to determine the width of the defective zones.

This sweeping, which can be obtained by any known type of remote control, is not perpendicular to the direction of movement of the gantry crane or the semifinished product, but rather is oblique, so as to avoid the projection of molten metal onto the uprights of the crane.

This oblique sweeping can be made continuous by alternating movement of the torch from one to the other side of the width or in sequence; each sequence is separated by periods when the torch describes a line parallel to the axis of the semifinished product; in this manner, a succession of lengthwise strips and oblique strips is obtained which allow better examination of the semifinished products.

The apparatus of the invention also includes a means for pick-up of the image of the surface provided by the torch or torches, and its transmission for some distance.

In fact, the direct on-site detection of defects of the semifinished products was formerly impossible because of the heat radiation of the semifinished products. Thus it is necessary to transmit the image of the weak points or defects to a point away from this site.

For that, a video camera or CCD (charge coupled device) camera (photodiode matrix network) is used, which generally is fixed on the gantry crane and the objective of which is centered on the point of application of the torch. This camera transmits the images to a screen so that the operator can follow the appearance of white spots as easily as if the semifinished product were being viewed directly.

This type of pick-up and retransmission is for the most part known. But what is of importance in the present invention is the possibility for the operator to continue to analyze the type, dimensions, and depth of the weak point or defect and to be able to then control the repair orders with perfect knowledge of cause. In fact, these are neither parasitic nor more or less fictive or unfaithful images of the semifinished products, as can be transmitted by the means of the prior art, but are actual images from which any deformation due to the system of detection in and of itself is excluded.

As these images are transient, and they evolve as a function of the position of the torch, it is necessary to store them. For that, the observer, upon viewing the screen, establishes a map representing the portion of surface which is examined and on which the detected defects are recorded, noting precisely their position and their dimensions as well as their type and their depth, which can be represented with the use of conventional signs or different colors. The recording can be made manually or better yet by suitable data processing means which are known.

This map is then given to the repairer who introduces it into the memory of a mechanical automatic scarfing device and the semifinished product is repaired as efficiently as in the prior art wherein the scarfing machine was guided visually by marking of the sites where it had to intervene.

The invention thus teaches simple means for detection and recording of weak points or defects on semifinished hot iron and steel industry products, which allow these either to be sent directly to the rolling unit, or toward repair or toward recycling, and at the same time alerts the steelmaker of anomalies in the casting before the casting sequence is even terminated.

The invention can be illustrated by the following example of use.

EXAMPLE

A slab of steel of dimensions 12×2.1×0.22 m having a temperature of 900 degrees C. was placed flat under a gantry crane which was moving at a speed of 20 m/minute. A blowtorch was affixed to the gantry crane so that the point of application was in the form of an ellipse with 90 mm large axis, a 50 mm small axis and 3 mm depth. This torch was moved parallel to the length of the slab, both at the center end on the edges.

The spots which appeared during application of the torch along the entire length of the semifinished product were picked up by an Ultricom video camera. The images transmitted to a remote screen 50 meters away from the site of detection allowed an observer to record the weak points or defects of the detection site as shown in FIG. 1 and to establish the map of distribution shown in FIG. 2. In FIG. 1, the image of the slab (1) is shown, on which are distinguishable the lengthwise strips of application of the torch, the edge strips (2) and (3) and the central strip (4).

Figure 2:
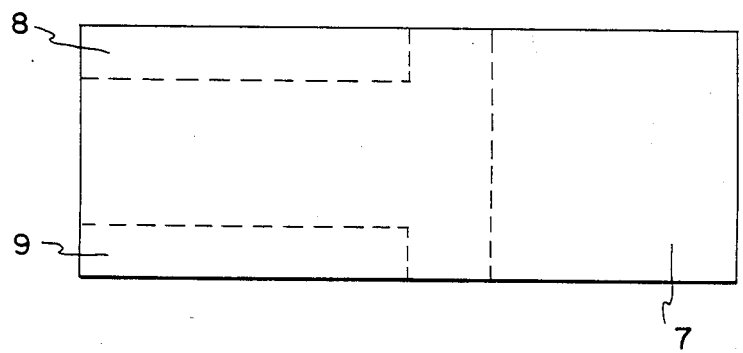
FIG. 2 is a plot of the surface shown in FIG. 1.

On each of these strips, zones (4) without defect or weak point, zones (5) with inclusions and defects of casting renewal, and zones (6) having tears at an angle have been observed. FIG. 2 shows the record of the inclusionary surface (7) to be repaired with the corresponding edge and the surfaces (8) and (9) near the edges where the tears must be eliminated.

This map was used by a scarfing machine and permitted the scarfing machine to carry out the repairs so that the flat product obtained by rolling shows no defect.

Figure 3:
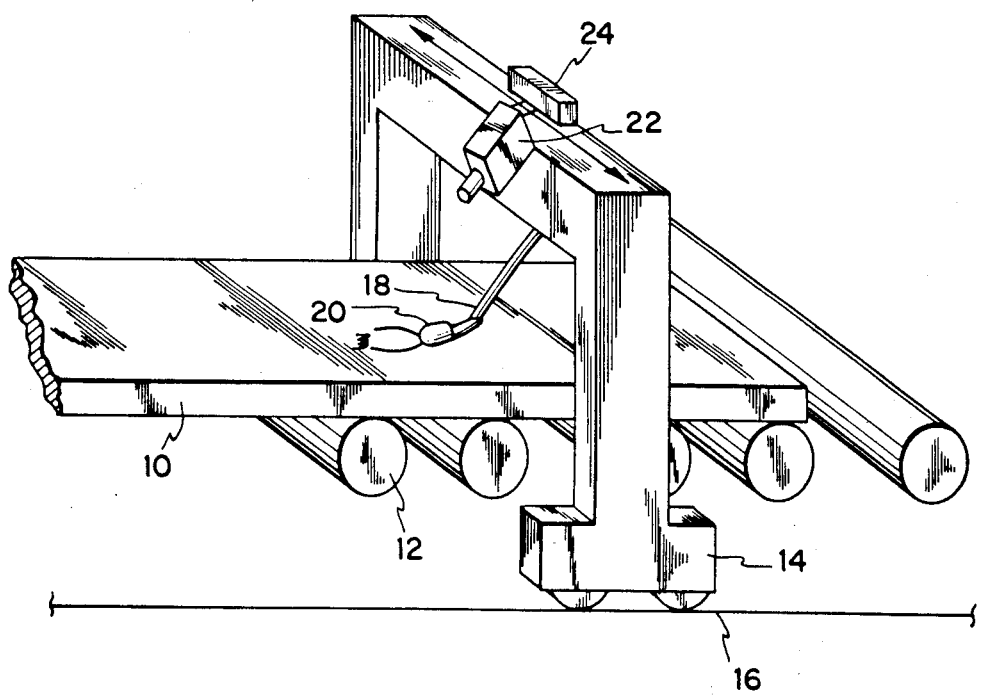
FIG. 3 is a schematic perspective view of an apparatus used to carry out the method of the invention.

FIG. 3 shows in greatly simplified form an apparatus used to record defects according to the method of the invention. A steel slab 10 is passed over rollers 12 while still hot. A gantry crane 14 movable on track 16 is positioned such that the steel slab passes under the crane. Mounted on the gantry crane is a blowtorch 18 having a head 20 at an angle which is adjustable with respect to the steel slab 10. Also mounted on the crane is a television camera 22 wired to a remote location, not shown. Both the blowtorch and the television camera are movable longitudinally across the crane in the direction of the arrows by adjustment of a cable, not shown, attached to mounting device 24.

What is claimed is:

1. A continuous method for the detection, recording and repair of defects and/or weak points of a hot semifinished iron or steel product prior to hot rolling, the method comprising:
   (a) locating an oxygen supplied blow torch adjacent a surface of the hot semi-finished product so that an oxygen-supplied flame from the torch is at a predetermined angle relative to the plane of the surface of said product;
   (b) moving the product at a predetermined rate of speed relative to the flame;
   (c) applying the oxygen-supplied flame to the surface of said product, which causes (1) the iron or steel at said surface to melt, (2) the molten metal to be removed to expose the underlying iron or steel in the semifinished product, and (3) a visual indication of the defects and/or weak points to appear;
   (d) transmitting a visual image of said surface to a location remote from the torch;
   (e) reproducing said image at said remote location and recording the position of said defects and/or weak points; and
   (f) repairing the defects and/or weak points prior to hot rolling said product.

2. Process as in claim 1, wherein the angle between the axis of the torch and the plane of the surface to be examined is between 5 and 15 degrees.

3. Process as in claim 1, wherein the speed of displacement of the application point of the torch is between 15 and 30 m/minute.

4. Process as in claim 1, wherein the application of the torch describes a line parallel to the lengthwise axis of the semifinished product.

5. Process as in claim 1, wherein the application point of the torch describes an oblique line in relation to the lengthwise axis of the semifinished product.

6. Process as in claim 1, wherein the application point of the torch by successive sequences describes a line which is parallel and a line which is oblique in relation to the lengthwise axis of the semifinished product.

* * * * *